United States Patent [19]

Chapman

[11] 4,211,781

[45] Jul. 8, 1980

[54] PROCESS FOR THE PREPARATION OF DUSTLESS QUINOXALINE-1,4-DIOXIDE ANIMAL FEED SUPPLEMENT PREMIXES

[75] Inventor: Kenneth G. Chapman, Groton, Conn.

[73] Assignee: Pfizer Inc., New York, N.Y.

[21] Appl. No.: 605,805

[22] Filed: Aug. 19, 1975

Related U.S. Application Data

[63] Continuation-in-part of Ser. No. 508,056, Sep. 23, 1974, abandoned.

[51] Int. Cl.$^2$ .......................... A61L 13/00; A23L 3/36
[52] U.S. Cl. ..................... 424/250; 426/532; 426/543; 426/623; 426/630; 426/635
[58] Field of Search ............... 424/250; 426/335, 532, 426/543, 623, 630, 635

[56] References Cited

U.S. PATENT DOCUMENTS

| | | | |
|---|---|---|---|
| 2,049,017 | 2/1935 | Musher | 426/543 X |
| 3,257,209 | 6/1966 | Lewis | 426/630 |
| 3,371,090 | 2/1968 | Johnston | 424/251 X |
| 3,468,667 | 9/1969 | Chandler et al. | 426/648 X |
| 3,617,299 | 11/1971 | Mattoon et al. | 426/635 |
| 3,752,812 | 8/1973 | Abushanab | 424/250 X |
| 3,759,912 | 9/1973 | Derungs | 424/250 |
| 3,798,222 | 3/1974 | Senning et al. | 424/250 X |

*Primary Examiner*—Dale R. Ore
*Attorney, Agent, or Firm*—Connolly and Hutz

[57] ABSTRACT

A process for the preparation of substantially dustless quinoxaline-1,4-dioxide animal feed supplement premixes is disclosed.

7 Claims, No Drawings

PROCESS FOR THE PREPARATION OF DUSTLESS QUINOXALINE-1,4-DIOXIDE ANIMAL FEED SUPPLEMENT PREMIXES

CROSS REFERENCE TO RELATED APPLICATIONS

This application is a continuation-in-part of Ser. No. 508,056, filed Sept. 23, 1974, now abandoned.

BACKGROUND OF THE INVENTION

Many quinoxaline-1,4-dioxides administered to animals are effective in the control of urinary tract and systemic infections, chronic respiratory disease in poultry and infectious sinusitis in turkeys such as disclosed in U.S. Pat. No. 3,371,090. Of special interest is their use in the control of swine dysentery. These anti-bacterial agents are useful in both prophylaxis and therapy. By controlling or eliminating many common bacterial infections which afflict animals, these agents also function as both growth and feed efficiency promotors. Quinoxaline-1,4-dioxide anti-bacterial agents have the structure

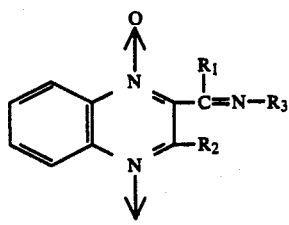

wherein each of $R_1$ and $R_2$ is individually selected from the group consisting of hydrogen and lower alkyl; $R_3$ is selected from the group consisting of

NH—CO—NH$_2$
NH—CS—NH$_2$
NH—C(NH)—NH$_2$
NHR$_4$
NHCOOR$_5$
NHCOR$_6$
OR$_7$

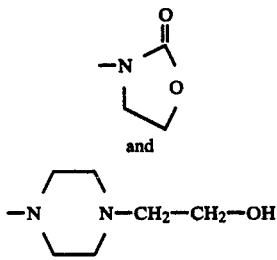

wherein
$R_4$ is selected from the group consisting of lower alkyl, phenyl, benzyl and hydroxyalkyl containing from 2 to 4 carbon atoms;
$R_5$ is selected from the group consisting of lower alkyl, hydroxyalkyl containing from 2 to 4 carbon atoms, and haloalkyl containing from 2 to 4 carbon atoms;
$R_6$ is selected from the group consisting of lower alkyl and phenyl; and $R_7$ is selected from the group consisting of hydrogen and lower alkyl. The term "lower alkyl" as used herein includes the branched-chain as well as the straight-chain radicals of those lower alkyl group having three or more carbon atoms. Particularly preferred as an anti-bacterial is 2-formyl-quinoxaline-1,4-dioxide carbomethoxy-hydrozone known by the common name of carbadox.

Carbadox is being supplied to the consumer as premix which is further blended with an aminal feed to produce an ultimate product containing a pharmaceutically effective concentration of carbadox. The composition of the premix varies depending upon the area of the world in which it is intended for consumption. The carrier is also varied with an effort made to use a material, usually farinaceous, which is readily available in the area in which it is to be consumed. Typical carbadox premixes contain about 85 to 98 percent carrier and anywhere from 2 to 12 percent carbadox. Up to about 1% by weight of silicon dioxide or 10% by weight of calcium carbonate may be used in addition to farinaceous materials. Also an effective amount of calcium propionate as a preservative, usually about 0.2% by weight, is sometimes added. Among the fairinaceous carriers are rice bran, corn germ meal, soybean meal, soybean grits, wheat middlings, corn gluten feed, soft phosphate rock, cornmeal, rapeseed meal and soybean mill run.

Because of the physical nature of the carbadox crystal, a nature it shares with other quinoxaline-1,4-dioxides, difficulties are encountered in the formulation of a dustfree premix containing a uniform amount of carbadox. Present processes to produce carbadox yield an extremely fine crystalline material with typically about 3% by weight smaller in size than 5 micrometers, 23 percent between 5 and 10 micrometers and 74 percent larger than 10 micrometers. This particle size distribution can, however be extremely deceiving since the carbadox crystal is very friable and tends with abrasion to be reduced greatly in size.

Because of the small particle size of carbadox relative to the carrier, any dust escaping from the blender in which the premix is formulated would be expected to be composed mostly of carbadox. Measurements have in fact shown that said escaped dust is about 93 percent carbadox. Though particles smaller than 10 micrometers are usually regarded as respirable, this presents no problem in the current application because all mixing is done in closed systems with dust collectors. Nevertheless, the escaping dust does create difficulty in producing a uniform formulation. The carbadox which is trapped in a dust collector, which in most instances is a bag house, is recycled back to the mixer. However 6 or 7 batches may be run before the collected material is removed, weighed, and recycled. As a result the initial mixtures will tend to be low in carbadox composition and the batch containing the recycled material high in carbadox concentration. Uniformity of composition requires, therefore, that even in a closed system the amount of dust generated in blending process be an absolute minimum.

The premix remains dusty even after it is removed from the blender and packaged for shipment. It is believed that some carbadox may actually be lost in shipment and it is known that some is definitely lost when the premix is formulated into a feed by the ultimate user. Again, uniformity of composition requires a stable, that is, dustless blend of carbadox and carrier. Furthermore, it is generally undesirable to market a product which contains or generates respirable dust even though no medical hazard may be immediately apparent.

Dustless quinoxaline-1,4-dioxide premixes are also extremely desirable because of their safety. The tendency of carbadox to explode is great. Its minimum ignition energy is extremely low and the crystal is highly flammable and self-sustaining in the absence of air. In stable, dustless premixes these dangers are not encountered. However, a hazard does exist whenever carbadox separates from its carrier. Stable premixes eliminate the possibility of baghouse fires and explosions in transit. Dusty premixes may not be shipped by air freight whereas the product of the current invention is sufficiently safe to be shipped by any mode of transportation.

SUMMARY OF THE INVENTION

The present invention is a process for the preparation of substantially dustless quinoxaline-1,4-dioxide animal feed supplement premix. The process comprises blending about 0.5 to about 2.0 percent and preferably about 1.0 to 1.25% of a suitable non-toxic oil, usually one with some nutritive value, such as soybean oil, corn oil, mineral oil and mixtures thereof with about 80 to 95 percent of an edible carrier which is usually farinaceous in nature such as soybean mill run, rice brans, soybean meal, soybean grits, corn germ meal, corn gluten feed, wheat middlings, rapeseed meal and mixtures thereof. Soft phosphate rock is also used as are blends of all the above with silicon dioxide and calcium carbonate. The non-toxic oil itself frequently contains an appropriate antioxidant such as calcium pripionate. Said mixture of carrier and oil is then blended with about 2 to 12 percent of pharmaceutically acceptable quinoxaline-1,4-dioxide anti-bacterial agent. Of particular interest as an anti-bacterial agent is 2-formyl-quinoxaline-1,4-dioxide carbomethoxyhydrozone. To the thoroughly blended mixture of oil, carrier and antibacterial agent is then added another 1.5 to 6.0 percent and preferably about 3.0 to 3.75 percent of said oil and the mixture again thoroughly blended. All of the above percentages refer to percent by weight composition in the final premix. The final concentration of oil in the premix should range from about 2 to about 8 percent and preferably from about 4 to about 5 percent.

DETAILED DESCRIPTION OF THE INVENTION

It has been found that stable premixes of quinoxaline-1,4-dioxide anti-bacterial agent used as animal feed supplements which have substantially no tendency to segregate, are free of respirable dust and are without the flammable and explosive properties of pure quinoxaline-1,4-dioxides may be formulated by the sequential oil addition process described above.

Particularly preferred are those premixes wherein said oil is soybean oil or mineral oil, and said oil contains a suitable antioxidant such as calcium propionate with soybean mill run, rapeseed meal, rice brans or soybean meal as carrier.

The addition of oil to reduce the amount of dust in animal feed supplements is known in the art. U.S. Pat. No. 3,468,667 discloses a product containing decalcium ortho phosphate, diammonium orthophosphate, ammonium dihydrogen phosphate and mixtures thereof also containing glyceryl lactopalmitate and a fatty acid or fatty acid salt wherein an oily liquid is added for the purpose of binding the mixture. Furthermore, it is obvious that increasing the amount of oil in any feed supplement including those of the instant invention will reduce the amount of dust contained therein. However, the addition of large amounts of oil for this purpose may yield a product with many undesirable properties such as poor flowability which makes the product difficult to mix and package.

It has now been discovered that in the manufacture of premixes especially those containing quinoxaline-1,4-dioxide anti-bacterial agents that the addition of oil in two portions, approximately 20 to 30 percent before the anti-bacterial agent and in particular those agents disclosed in U.S. Pat. No. 3,371,090 is added to the carrier and the balance of the oil after the anti-bacterial agent is added is significantly more effective in producing a dustless feed supplement premix than the addition of oil in a single batch either before or after the introduction of said antibacterial agent. In particular, it has been found that the use of approximately 2 to 8 percent and preferably about 4 to 5 percent oil added in such a fashion so that approximately 10 to 60 and preferably 20 to 30 percent of said oil is coated onto the carrier before the addition of the anti-bacterial agent and the balance after the anti-bacterial agent is added is exceptionally effective in eliminating respirable dust from the feed supplement premix. In a similar experiment with premix containing 10% carbadox it was found that the addition of 0.75% oil before and an equal amount after the addition of carbadox was approximately nine times more effective than adding 1.5% oil before the addition of the carbadox. In one experiment with a supplement wherein the ingoing premix contained 2.2% carbadox, it was found that the addition of 0.75% oil before the carbadox and 2.25% after the carbadox was up to about forty times as effective in reducing the amount of respirable dust than the addition of the same amount of oil before the carbadox was added. Also it can be estimated from these experiments that the addition of 3 percent oil is up to 50 times more effective than the addition of 1.5 percent oil in the elimination of respirable dust. The product containing 5 percent oil has good flow properties. The addition of amounts of oil in excess of about 8% reduces the flowability of the premix which makes it difficult to blend and package. It is believed that the first increment of oil added forms a coating on the surface of the carrier to which the carbadox adheres and that the second increment of oil then covers the carbadox and prevents the friable crystal from breaking down due to abrasion thus preventing segregation of the mixture. We do not however wish to be bound by this interpretation.

EXAMPLE I

Direct Formulation of Carbadox Premix

Pre-milled soybean mill run (7,583.7 lbs.) is weighed and added to a mixer. Soybean oil (60 lbs.) is added and the mixer run until the soybean mill run is uniformly coated with oil. Feed grade carbadox (176.3 lbs.) is then added and the mixer run again to uniformly blend the carbadox into the mixture. Soybean oil (180 lbs.) is then added and the batch mixed for a pre-set time until homogenous to yield a carbadox premix which is substantially dust free having a concentration of 10 grams of carbadox per pound.

This premix formulation is suitable for use in the United States. In similar fashion the following carbadox premixes may be formulated for ultimate consumption in other countries, the differences being in typical carrier materials most available at the cheapest price in the respective countries. Soybean oil (3%) is incorporated in each of these with 0.75% added before the carbadox and 2.25% after.

Premixes other than those listed in the table which contain quinoxaline-1,4-dioxide anti-bacterial agents may also be formulated in similar fashion.

|     |            | Carbadox (%) | Carrier             | Amount (%) | Other Ingredients |
| --- | ---------- | ------------ | ------------------- | ---------- | ----------------- |
| 1.  | Japan      | 11.0         | Rice Brans          | 89.0       | None              |
| 2.  | Korea      | 2.20         | Corngerm Meal       | 97.8       | None              |
| 3.  | Taiwan     | 11.0         | Soybean Meal        | 89.00      | None              |
| 4.  | Germany    | 4.0          | Soybean Grits       | 96.0       | None              |
| 5.  | France     | 5.00         | Soybean Meal        | 94.0       | $SiO_2$ 1.0%      |
| 6.  | Greece     | 10.00        | Soybean Meal        | 89.0       | $SiO_2$ 1.0%      |
| 7.  | Italy      | 1.00         | Soybean Meal        | 98.0       | $SiO_2$ 1.0%      |
| 8.  | Spain      | 4.00         | Soybean Meal        | 95.0       | $SiO_2$ 1.0%      |
| 9.  | Brazil     | 5.00         | Soybean Meal        | 95.0       | None              |
| 10. | Argentina  | 2.10         | Wheat Middlings     | 97.90      | None              |
| 11. | Canada     | 2.43         | Corn Gluten Feed    | 97.57      | None              |
| 12. | Mexico     | 1.21         | Soft Rock Phosphate | 33.65      | None              |
|     |            |              | Wheat Middlings     | 65.14      |                   |
| 13. | Costa Rica | 1.10         | Corn Meal           | 88.70      | $CaCO_3$ 10.0%    |
|     |            |              |                     |            | Ca Propionate 0.2% |

EXAMPLE II

Formulation of Carbadox Premix Through a Pre-Blend

Pre-milled soybean mill run (645.2 lbs.) is placed in a mixer. Soybean oil (60.0 lbs.) is added and the mixer run for a pre-set time until the soybean oil uniformly coats the soybean mill run. Feed grade carbadox (176.3 lbs.) is then added and the mixer run for a pre-set time until the blend is homogenous. This product, known as a pre-blend, is then stored until such time as it is desired to make the premix.

To make the premix, said pre-blend (881.5 lbs.) is added to a mixer along with pre-milled soybean mill run (6.938.5 lbs.) and the mixer run for a pre-set time until the blend is homogenous. Soybean oil (180.0 lbs.) is then added and the mixer run for a pre-set time until the oil uniformly coats the carrier and the carbadox. This premix (8,000 lbs.) is substantially dustless, contains 10 grams of carbadox per pound and is a formulation suitable for use in the United States.

In similar fashion the premixes of Example I may be prepared through pre-blends.

EXAMPLE III

Determination of the Percentage of Carbadox in Dust

An apparatus was constructed consisting of a 20 gallon drum with a 6"×4" elliptical hole cut in one end resting in a cradle which could be rocked by an electric motor at various rates. When the drum is charged with the carbadox premix, this apparatus simulates the dust generated as a bag of premix is emptied. The drum itself empties into a bin hopper similar to that used by feed manufacturers.

A premix (45 kilos) prepared by the method of Example II containing 10% carbadox and no oil was placed in the drum and the cover fastened on. Three Bendix Model C115 Air Sampling Probes were placed at a distance of 4 inches from the center of the anticipated dust cloud. This probe simulates human inspiration rates and velocities. The total inspiration rate is 22 liters per minute. They also separate particles less than and greater than 10 microns, those smaller than 10 microns being generally regarded as respirable. The air sampling probes were turned on as was the rocking cradle and the sample dumped over a 45 minute period. The dust was collected from each of the probes weighed and the carbadox concentration determined by differential pulse polarography. The lowest limit of easily detected carbadox in this assay procedure is 0.1 micrograms. The following results were obtained:

| Probe (3) | Respirable Dust Carbadox Weight/Dust Weight | % Carbadox | Non Respirable Dust Carbadox Weight/Dust Weight | % Carbadox |
| --- | --- | --- | --- | --- |
| 1 | No sample collected, probe obstructed | | | |
| 2 | 4.1 mg/4.3 mg | 95.5% | 31.2 mg/33.1 mg | 94.3% |
| 3 | 2.8 mg/2.9 mg | 96.5% | 26.0 mg/28.4 mg | 92.3% |

EXAMPLE IV

Effect of Oil Addition on Various Premixes

The premixes of this experiment were formulated in 100 pound batches in an AMF Glen mixer by first adding an appropriate amount of carrier to the mixer, blending it with the indicated amount of oil and carbadox and running the mixture until a homogenous blend was obtained.

The dustiness of the mixtures were determined by the method of Example III with the Bendix air samplers placed at a distance of 4, 20 and 30 inches from the center of the visible dust cloud formed at the dumping site.

A plus sign indicates that a positive analytical response was obtained but that the concentration was less than 0.1μ. ND incidates that no analytical response whatsoever was observed.

The data indicate that the decrease in dustiness with increasing oil concentration is non-linear and that virtually optimum results are obtained at about a 3% oil concentration. Above this percentage, the flowability of the premix is impaired.

| % Carbadox | Carrier | % Oil | Probe → | Carbadox Dust (Micrograms) | | | | | |
|---|---|---|---|---|---|---|---|---|---|
| | | | | Respirable | | | Non-Respirable | | |
| | | | | 1 | 2 | 3 | 1 | 2 | 3 |
| 1% | Soybean Meal | 0 | | 36 | 6.9 | 5.2 | 138 | 69 | 51 |
| 10% | Soybean Meal | 0 | | 30 | 26 | 5 | 1300 | 56 | 188 |
| 10% | Soybean Meal | 1.5 | | 5.2 | 2.7 | 1.7 | 146 | 74 | 32 |
| 10% | Soybean Meal | 3.0 | | + | + | + | 3.8 | 1.9 | 1.2 |
| 2.2% | Soy Mill Run | 0 | | .6 | .4 | .1 | 49 | 20 | 9 |
| 2.2% | Soy Mill Run | 0.75 | | + | ND | ND | 8 | 2 | 12 |
| 2.2% | Soy Mill Run | 1.5 | | .3 | .2 | .1 | 3.2 | 1.6 | 1.2 |
| 2.2% | Soy Mill Run | 3.0 | | + | .12 | + | 1.5 | .3 | 4.0 |
| 2.43% | Corn Gluten | 0 | | 5.5 | 2.0 | 2.5 | 238 | 120 | 114 |
| 2.43% | Corn Gluten | 3.0 | | .1 | .1 | .1 | 4.2 | 1.3 | 1.1 |

EXAMPLE V

Effect of Incremental Oil Addition on Premixes

The dustiness of premixes formulated in 100 lb. batches by the method of Example I was measured by the method of Example IV. The following results were obtained.

| % Carbadox | Carrier | % Soybean Oil | Probe → | Carbadox Dust (Micrograms) | | | | | |
|---|---|---|---|---|---|---|---|---|---|
| | | | | Respirable | | | Non-Respirable | | |
| | | | | 1 | 2 | 3 | 1 | 2 | 3 |
| 10 | Soybean Meal | 1.5 | | 5.2 | 2.7 | 1.7 | 146 | 74 | 32 |
| 10 | Soybean Meal | 0.75 + 0.75 | | 0.7 | 0.2 | 0.3 | 83 | 26 | 42 |

EXAMPLE VI

The following premixes were prepared by the method of Example I. In each instance, one-fourth of the oil was added to the carrier before the carbadox and three-fourths after the addition of the carbadox.

| INGREDIENT | % | % | % |
|---|---|---|---|
| Carbadox (wet cake)* | 13.33 | 3.33 | 6.67 |
| Soybean oil | 5.00 | 5.00 | 5.00 |
| Calcium propionate | 0.50 | 0.125 | 0.25 |
| Rapeseed meal | 81.17 | 91.54 | 88.08 |
| Carbadox (wet cake)* | 6.67 | 3.33 | 3.33 |
| Soybean oil | 4.00 | 4.00 | 5.00 |
| Calcium propionate | 0.25 | 0.125 | 0.125 |
| Soybean mill run | 89.08 | 92.54 | 91.54 |

*Approximately 75% carbadox; 25% water. Dry carbadox equivalent may be calculated with the following formula:
grams carbadox/lb activity = % carbadox wet cake × 0.75 × 454 grams.

What is claimed is:

1. A process for the production of a substantially dustless animal feed supplement premix containing an anti-bacterial quinoxaline-1,4-dioxide, said process comprising:
 (a) blending about 0.5 to about 2.0% of a non-toxic oil with about 80 to about 95% of an edible carrier;
 (b) mixing said blend with about 2 to about 12% of a pharmaceutically acceptable quinoxaline-1,4-dioxide antibacterial agent; and
 (c) adding to and blending into the mixture obtained in step (b) about 1.5 to about 6.0% of said oil so that the total amount of oil added is in the range of about 2 to about 8%
 wherein all percentages refer to the weight percentage of said component in said premix.

2. The process of claim 1 wherein the amount of oil added in step (a) is from about 1.0 to 1.25% and that added is step (c) is from about 3.0 to 3.75%.

3. The substantially dustless animal feed supplement premix obtained by the process of claim 1.

4. The substantially dustless animal feed supplement premix obtained by the process of claim 2.

5. The process of claim 1 wherein said oil is selected from the group consisting of soybean oil, corn oil and mineral oil.

6. The process of claim 5 wherein said oil is soybean oil.

7. The process of claim 1 wherein said edible carrier is selected from the group consisting of soybean mill run, rice brans, soybean meal, soybean grits, rapeseed meal, cornmeal, corn germ meal, corn gluten feed, wheat middlings, soft phosphate rock, mixtures thereof and admixtures thereof with silicon dioxide and calcium carbonate.

* * * * *

UNITED STATES PATENT AND TRADEMARK OFFICE
CERTIFICATE OF CORRECTION

PATENT NO. : 4,211,781     Page 1 of 2
DATED : July 8, 1980
INVENTOR(S) : Kenneth G. Chapman It is certified that error appears in the above-identified patent and that said Letters Patent are hereby corrected as shown below:

Column 1 first generic structure - should be

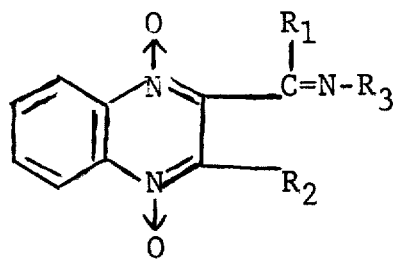

Column 2 line 4 change "group" to -- groups --.

Column 2 line 7 change "bomethoxy-hydrozone" to -- bomethoxyhydrozone --.

Column 2 line 24 change "fairinaceous" to -- farinaceous --.

Column 2 line 37 change ", however" to -- , however, --.

Column 3 line 32 change "pripionate" to -- propionate --.

UNITED STATES PATENT AND TRADEMARK OFFICE
CERTIFICATE OF CORRECTION

PATENT NO. : 4,211,781

DATED : July 8, 1980

INVENTOR(S) : Kenneth G. Chapman

It is certified that error appears in the above-identified patent and that said Letters Patent are hereby corrected as shown below:

Column 3 line 63 change "decalcium" to -- dicalcium --.

Column 3 line 64 change "ortho phosphate" to -- orthophosphate --.

Column 5 line 51 change "(6.938.5 lbs.)" to -- (6,938.5 lbs.) --.

Signed and Sealed this

Ninth Day of December 1980

[SEAL]

*Attest:*

SIDNEY A. DIAMOND

*Attesting Officer*     *Commissioner of Patents and Trademarks*